United States Patent
Kho et al.

(10) Patent No.: US 10,535,184 B2
(45) Date of Patent: Jan. 14, 2020

(54) ULTRASONIC IMAGING APPARATUS AND CONTROL METHOD THEREOF

(71) Applicant: SAMSUNG ELECTRONICS CO., LTD., Suwon-si (KR)

(72) Inventors: Young Ihn Kho, Seoul (KR); Hee Sae Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 311 days.

(21) Appl. No.: 14/902,905

(22) PCT Filed: Jul. 4, 2014

(86) PCT No.: PCT/KR2014/006007
§ 371 (c)(1),
(2) Date: Jan. 5, 2016

(87) PCT Pub. No.: WO2015/002498
PCT Pub. Date: Jan. 8, 2015

(65) Prior Publication Data
US 2017/0249777 A1    Aug. 31, 2017

(30) Foreign Application Priority Data

Jul. 5, 2013   (KR) .................. 10-2013-0078794

(51) Int. Cl.
*A61B 8/00* (2006.01)
*A61B 8/08* (2006.01)
(Continued)

(52) U.S. Cl.
CPC .............. *G06T 15/08* (2013.01); *A61B 8/463* (2013.01); *A61B 8/466* (2013.01); *A61B 8/483* (2013.01);
(Continued)

(58) Field of Classification Search
USPC ........................... 345/419, 424, 426
See application file for complete search history.

(56) References Cited

U.S. PATENT DOCUMENTS 7,194,117 B2 *   3/2007  Kaufman ............... A61B 5/055
                                                         378/41
7,940,268 B2 *   5/2011  Zhou ..................... G06T 15/506
                                                         345/419
(Continued)

FOREIGN PATENT DOCUMENTS

CN    101357077 A    2/2009
CN    102695458 A1   9/2012
(Continued)

OTHER PUBLICATIONS

Communication dated Jan. 20, 2017 issued by the European Patent Office in counterpart European Patent Application No. 14819625.6.
(Continued)

*Primary Examiner* — Sing-Wai Wu
(74) *Attorney, Agent, or Firm* — Sughrue Mion, PLLC

(57) ABSTRACT

Disclosed herein are an ultrasonic imaging apparatus and a control method thereof. The ultrasonic imaging apparatus includes: an ultrasonic collector configured to collect ultrasonic waves from an object; a volume data generator configured to generate volume data based on the ultrasonic waves; and an image processor configured to perform volume rendering on the volume data with reference to a texture image, wherein a translucency property and multi-layer tissue of the object are reflected to each texel of the texture image.

8 Claims, 9 Drawing Sheets

(51) Int. Cl.
  *G01S 15/89* (2006.01)
  *G06T 15/04* (2011.01)
  *G06T 15/08* (2011.01)
  *G06T 19/20* (2011.01)
(52) U.S. Cl.
  CPC .............. *A61B 8/5207* (2013.01); *A61B 8/54* (2013.01); *G01S 15/8993* (2013.01); *G06T 15/04* (2013.01); *G06T 19/20* (2013.01); *G06T 2210/41* (2013.01); *G06T 2215/16* (2013.01); *G06T 2219/2012* (2013.01)

(56) References Cited

U.S. PATENT DOCUMENTS

| | | | | |
|---|---|---|---|---|
| 8,049,752 | B2* | 11/2011 | Yang | G06T 15/08 345/420 |
| 8,160,315 | B2* | 4/2012 | Hayashi | A61B 8/06 382/128 |
| 8,948,485 | B2* | 2/2015 | Tsujita | A61B 8/0808 382/128 |
| 9,734,621 | B2* | 8/2017 | Kuga | G06T 15/08 |
| 2001/0031920 | A1 | 10/2001 | Kaufman et al. | |
| 2004/0070582 | A1 | 4/2004 | Smith et al. | |
| 2005/0091672 | A1 | 4/2005 | Debique et al. | |
| 2005/0264578 | A1 | 12/2005 | Engel et al. | |
| 2007/0014446 | A1 | 1/2007 | Sumanaweera et al. | |
| 2007/0103465 | A1* | 5/2007 | Barenbrug | G06T 15/005 345/426 |
| 2008/0259080 | A1 | 10/2008 | Masumoto et al. | |
| 2008/0260227 | A1* | 10/2008 | Hayashi | A61B 8/06 382/131 |
| 2012/0087564 | A1* | 4/2012 | Tsujita | A61B 8/0808 382/131 |
| 2012/0095341 | A1* | 4/2012 | Shiki | A61B 8/06 600/443 |
| 2012/0327198 | A1 | 12/2012 | Tsukagoshi et al. | |
| 2013/0150719 | A1 | 6/2013 | Orderud | |
| 2013/0271455 | A1* | 10/2013 | Tsujita | A61B 8/0866 345/419 |
| 2016/0030007 | A1* | 2/2016 | Tsujita | G06T 15/08 600/438 |
| 2016/0038124 | A1* | 2/2016 | Tsujita | A61B 8/466 600/437 |

FOREIGN PATENT DOCUMENTS

| | | |
|---|---|---|
| CN | 103156638 A | 6/2013 |
| EP | 2 441 389 A1 | 4/2012 |
| JP | 2009-291295 A | 12/2009 |
| JP | 2010-240409 A | 10/2010 |
| JP | 4628645 B2 | 2/2011 |
| KR | 10-2001-0113840 A | 12/2001 |
| KR | 10-2002-0002484 A | 1/2002 |
| KR | 10-0738107 B1 | 7/2007 |

OTHER PUBLICATIONS

Communication dated Oct. 13, 2014 issued by the International Searching Authority in counterpart International Application PCT/KR2014/006007 (PCT/ISA/210).

Mark S. Sklansky et al; "Real-time 3-Dimensional Fetal Echocardiography With an Instantaneous Volume-Rendered Display"; Journal of Ultrasound Med., Feb. 1, 2004; vol. 23; No. 2; pp. 283-289.

Aaron Fenster et al; "Three-dimensional ultrasound scanning"; Interface Focus; Jun. 1, 2011; vol. 1; No. 4; pp. 503-519.

Communication dated Aug. 23, 2017 issued by the Korean Intellectual Propery Office in counterpart Korean Application No. 10-2013-0078794.

Communication dated Jan. 29, 2018 by the State Intellectual Property Office of P.R. China in counterpart Chinese Patent Application No. 201480038568.0.

Communication dated Feb. 26, 2018 by the Korean Intellectual Property Office in counterpart Korean Patent Application No. 10-2013-0078794.

Communication dated Apr. 11, 2018 by the Korean Intellectual Property Office in counterpart Korean Patent Application No. 10-2013-0078794.

Communication dated Aug. 23, 2017 issued by the Korean Intellectual Property Office in counterpart Korean Application No. 10-2013-0078794.

Communication dated Sep. 5, 2018, issued by the State Intellectual Property Office of P.R. China in counterpart Chinese Application No. 201480038568.0.

\* cited by examiner

[Fig. 1]
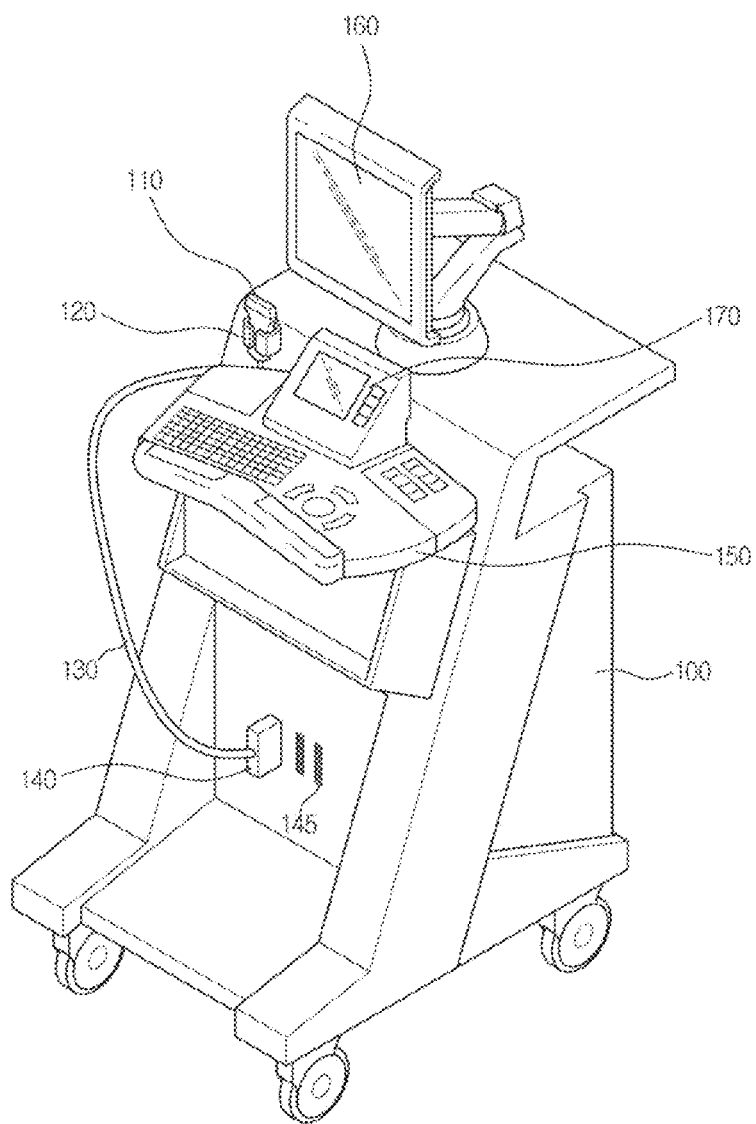

[Fig. 2]
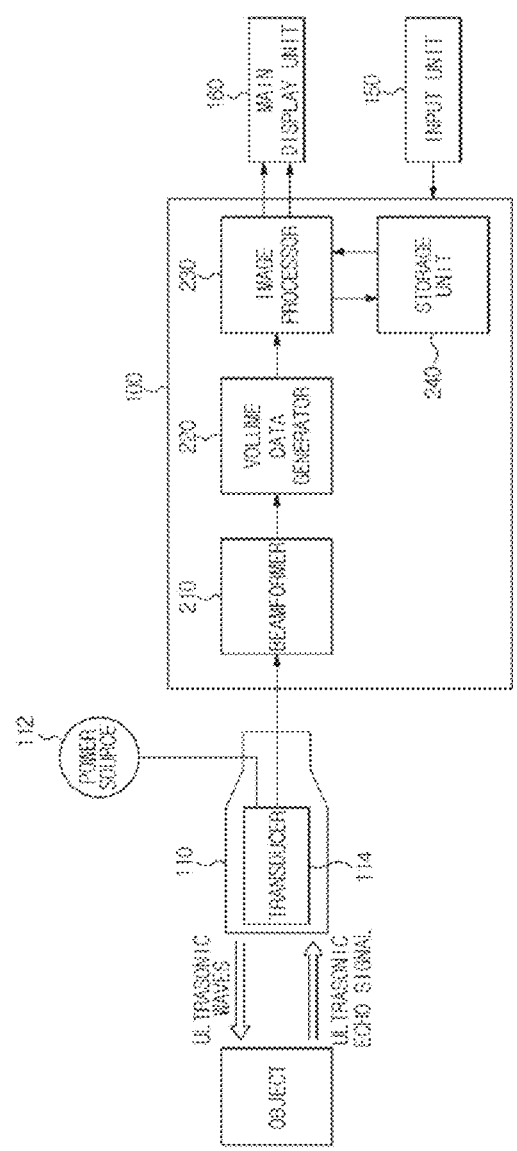

[Fig. 3]
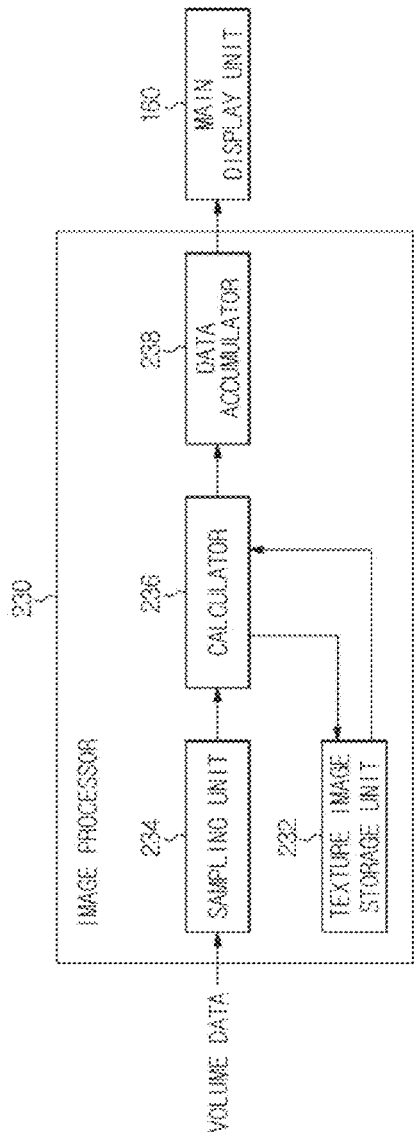
[Fig. 4]
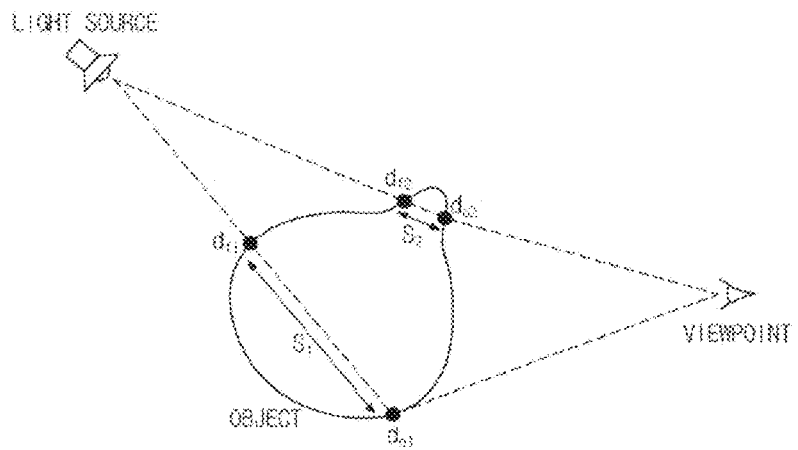

[Fig. 5]
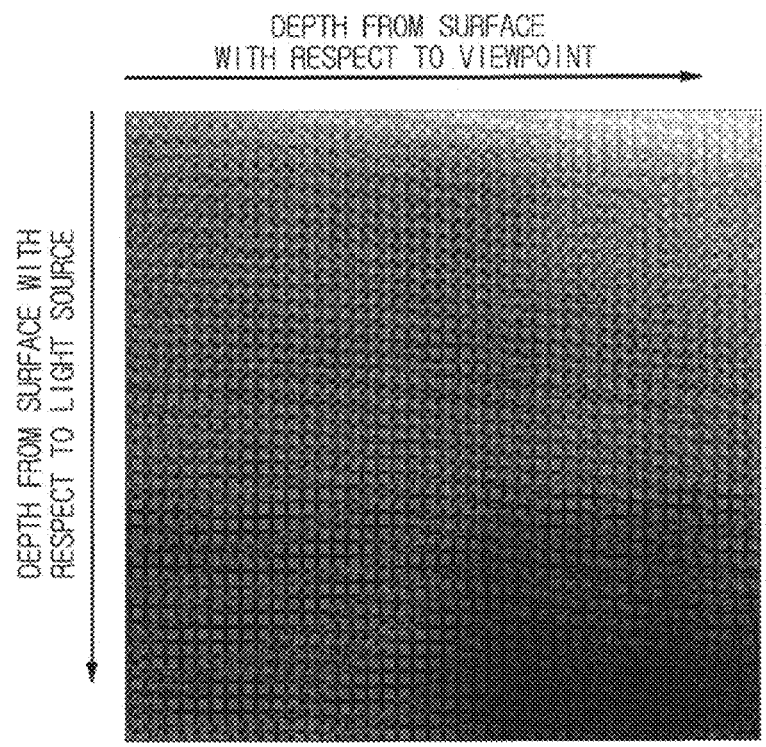
[Fig. 6]
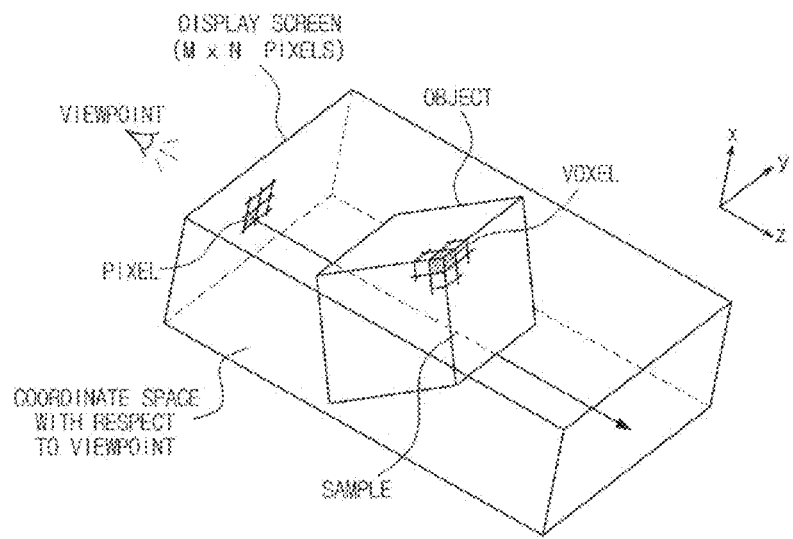

[Fig. 7]
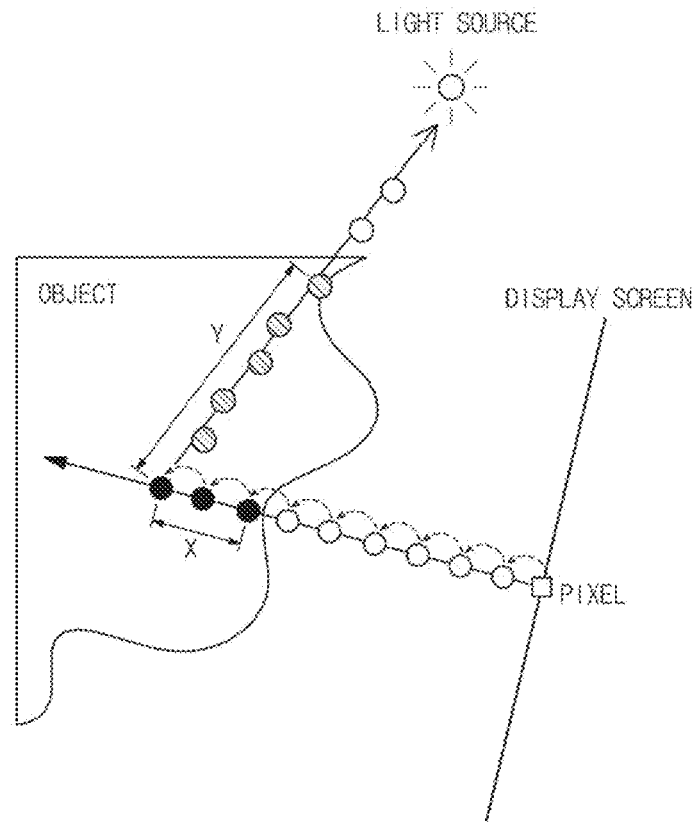
[Fig. 8a]
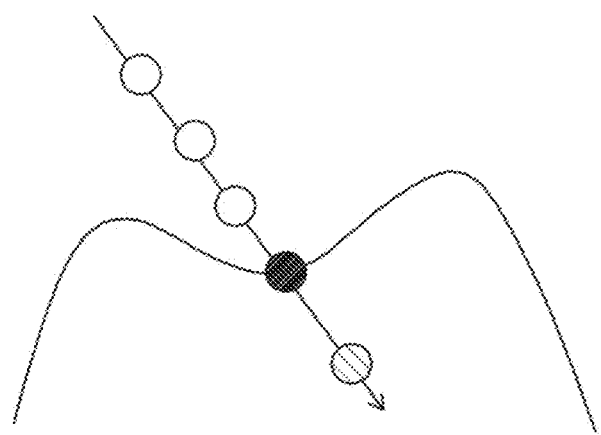

[Fig. 8b]
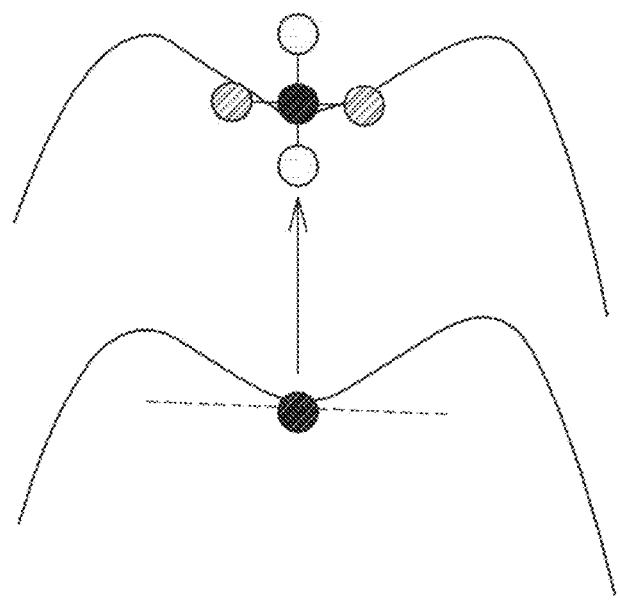
[Fig. 8c]
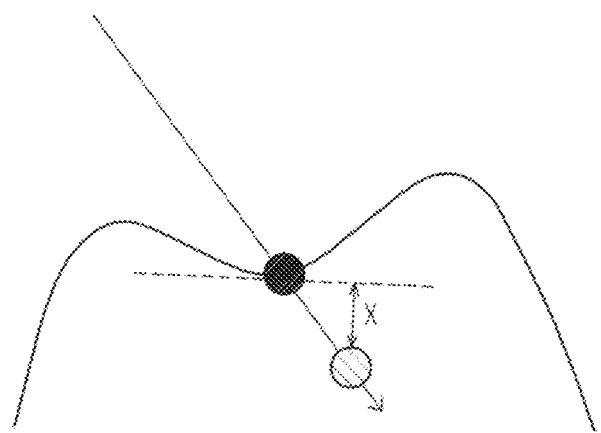

[Fig. 9]
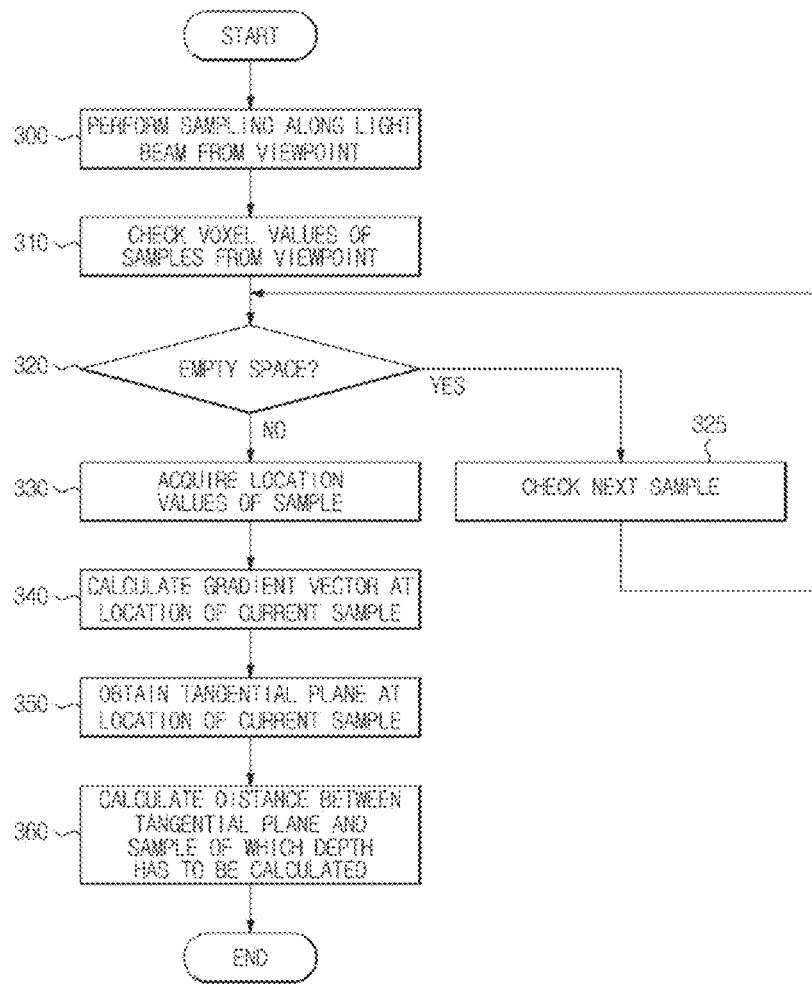
[Fig. 10a]
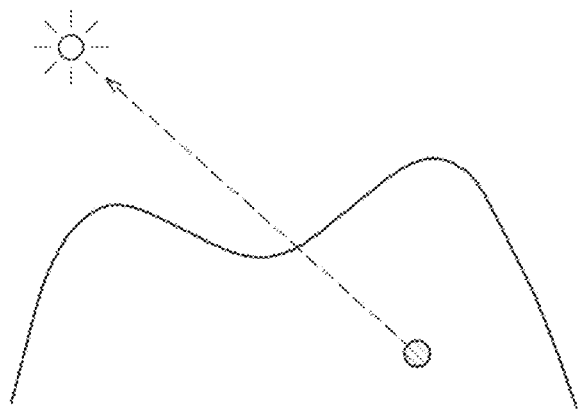

[Fig. 10b]
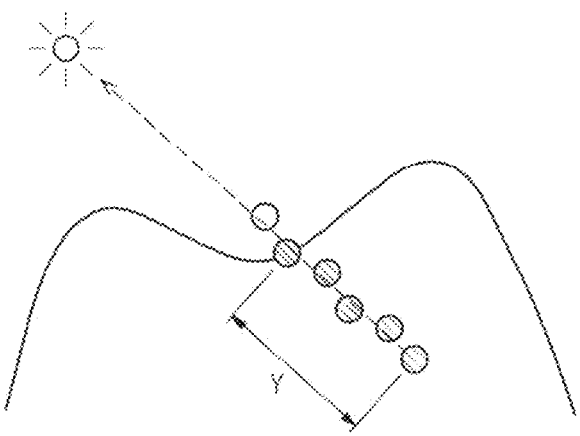
[Fig. 11]
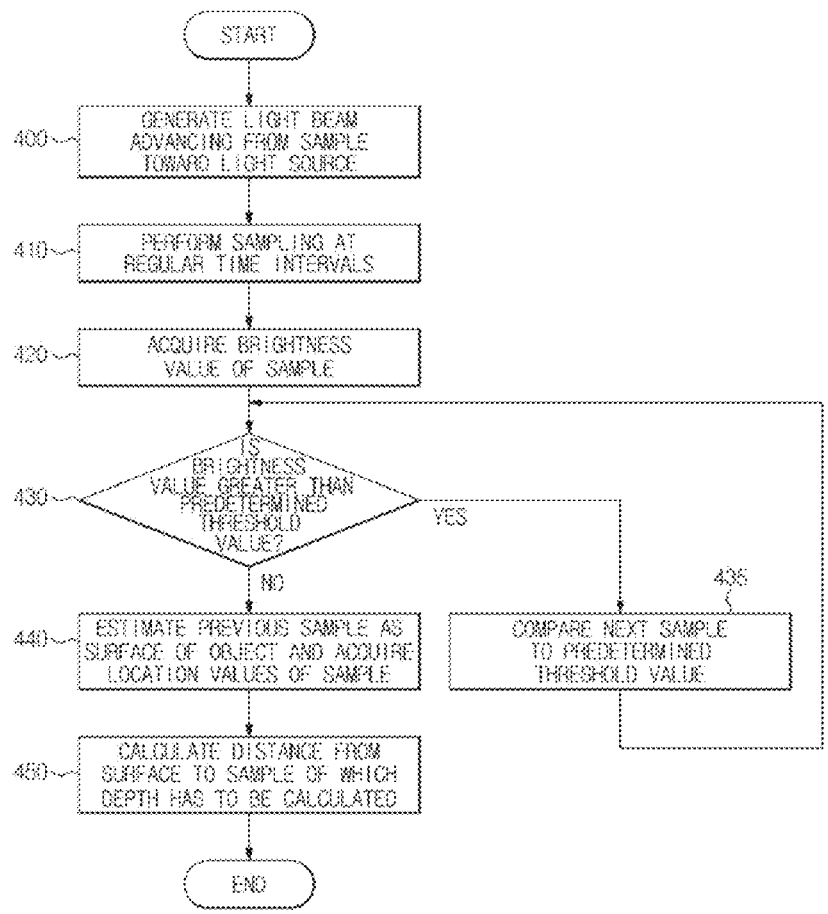

[Fig. 12]
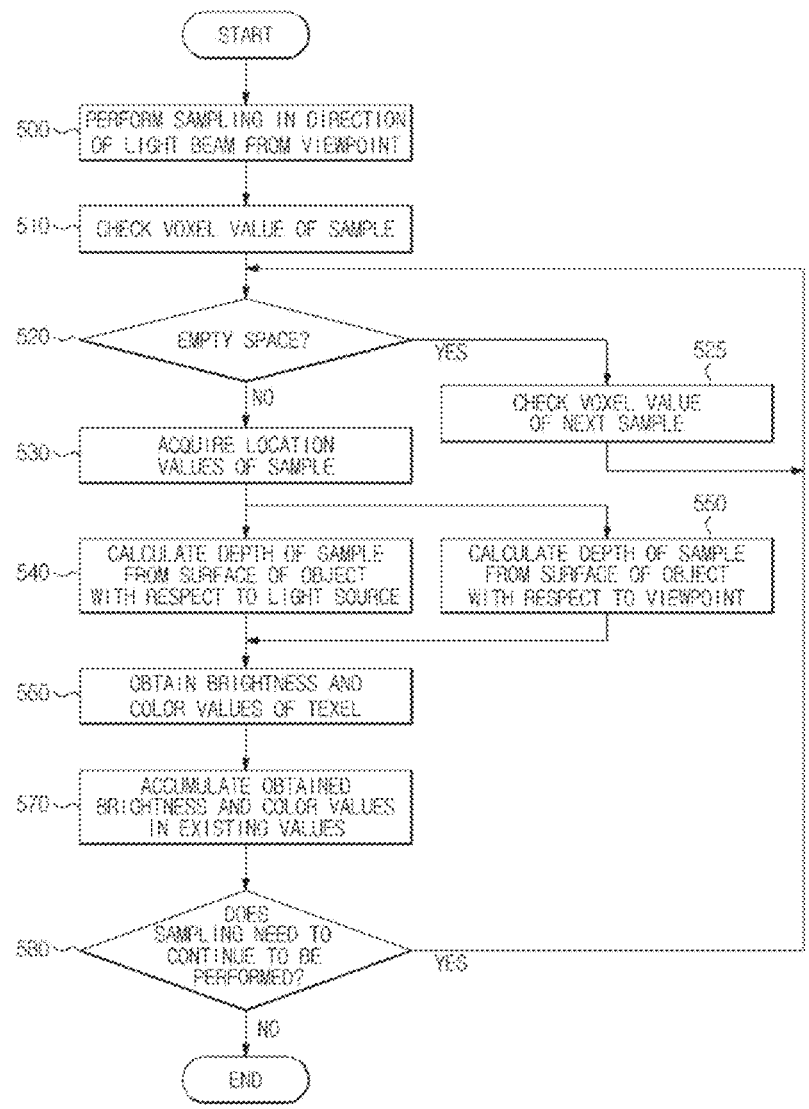

ULTRASONIC IMAGING APPARATUS AND CONTROL METHOD THEREOF

TECHNICAL FIELD

Embodiments of the present invention relate to an ultrasonic imaging apparatus and a control method thereof.

BACKGROUND ART

An ultrasonic imaging apparatus emits ultrasonic signals towards a specific part of a subject (e.g., a human body) from the skin surface of the subject, and receives ultrasonic signals (that is, ultrasonic echo signals) reflected from the specific part of the subject so as to non-invasively acquire section images about soft tissue or images about blood vessels based on information about the ultrasonic echo signals.

Compared to other imaging apparatuses including an X-ray imaging apparatus, a Computerized Tomography (CT) scanner, a Magnetic Resonance Image (MRI) apparatus, and a radiographic diagnosis system, the ultrasonic imaging apparatus is a low-priced apparatus having a small size, can display images in real time, and have high safety since there is no risk for patients to be exposed to radiation such as X-rays. For the advantages, the ultrasonic imaging apparatus is widely used to diagnose the heart, breasts, abdomen, urinary organs, uterus, etc.

In general, an ultrasonic imaging apparatus includes a main body to accommodate main components of the ultrasonic imaging apparatus, an ultrasonic collector to transmit and receive ultrasonic waves, a control panel including various switches and keys through which commands for manipulating the ultrasonic imaging apparatus are input, and a display to display the results of ultrasonic diagnosis as images.

A method in which the ultrasonic imaging apparatus performs ultrasonography on a subject is as follows. First, an operator holds the ultrasonic collector with his/her one hand to move the ultrasonic collector while keeping the ultrasonic collector in contact with the skin surface of a subject, and manipulates the control panel with the other hand to perform ultrasonography. An ultrasonic image obtained by the ultrasonography is displayed in real time through the display so that the operator can diagnose the state of the subject.

However, since ultrasonic images obtained by ultrasonography are monochrome images due to the physical properties of the ultrasonic imaging apparatus, there is limitation in representing the inner structure of a subject realistically. In order to overcome the limitation, a method of producing 3-dimensional (3D) color ultrasonic images based on arbitrarily selected colors has been developed. However, the method still has a problem that reality of images is low since the images are not based on the real colors of a subject. Particularly, when producing 3D ultrasonic images of the fetus, the method results in lower reality than when producing images of the heart, breasts, etc.

DISCLOSURE OF INVENTION

Technical Problem

Therefore, it is an aspect of the present invention to provide an ultrasonic imaging apparatus for producing a realistic 3-dimensional (3D) image by performing rendering with reference to a texture image to which a translucency property or multi-layer tissue of a subject has been reflected, and a control method of the ultrasonic imaging apparatus.

Additional aspects of the invention will be set forth in part in the description which follows and, in part, will be obvious from the description, or may be learned by practice of the invention.

Solution to Problem

In accordance with one aspect of the present invention, an ultrasonic imaging apparatus includes: an ultrasonic collector configured to collect ultrasonic waves from an object; a volume data generator configured to generate volume data based on the ultrasonic waves; and an image processor configured to perform volume rendering on the volume data with reference to a texture image, wherein a translucency property and multi-layer tissue of the object are reflected to each texel of the texture image.

In accordance with another aspect of the present invention, an ultrasonic imaging apparatus includes: an ultrasonic collector configured to collect ultrasonic waves from an object; a volume data generator configured to generate volume data based on the ultrasonic waves; and an image processor configured to perform volume rendering on the volume data with reference to a texture image, wherein a translucency property of the object is reflected to each texel of the texture image.

In accordance with another aspect of the present invention, An ultrasonic imaging apparatus includes: an ultrasonic collector configured to collect ultrasonic waves from an object; a volume data generator configured to generate volume data based on the ultrasonic waves; and an image processor configured to perform volume rendering on the volume data with reference to a texture image, wherein multi-layer tissue of the object is reflected to each texel of the texture image.

In accordance with another aspect of the present invention, a control method of an ultrasonic imaging apparatus includes: collecting ultrasonic waves from an object; generating volume data based on the ultrasonic waves; and performing volume rendering on the volume data with reference to a texture image, wherein a translucency property and multi-layer tissue of the object are reflected to each texel of the texture image.

In accordance with another aspect of the present invention, a control method of an ultrasonic imaging apparatus includes: collecting ultrasonic waves from an object; generating volume data based on the ultrasonic waves; and performing volume rendering on the volume data with reference to a texture image, wherein a translucency property of the object is reflected to each texel of the texture image.

In accordance with another aspect of the present invention, a control method of an ultrasonic imaging apparatus includes: collecting ultrasonic waves from an object; generating volume data based on the ultrasonic waves; and performing volume rendering on the volume data with reference to a texture image, wherein multi-layer tissue of the object is reflected to each texel of the texture image.

Advantageous Effects of Invention

According to the ultrasonic imaging apparatus and the control method thereof as described above, the following effects can be obtained.

By rendering volume data after reflecting a translucency property and multi-layer tissue of a subject to the volume data, it is possible to control and produce a realistic image such that it looks close to the real structure of the subject.

Particularly, when the ultrasonic imaging apparatus is used in gynecological diagnosis, the ultrasonic imaging apparatus may display the fetus's figure realistically, which leads to improvement of emotional stability and mental satisfaction of a pregnant woman and her family.

BRIEF DESCRIPTION OF DRAWINGS

These and/or other aspects of the invention will become apparent and more readily appreciated from the following description of the embodiments, taken in conjunction with the accompanying drawings of which:

FIG. 1 is a perspective view of an ultrasonic imaging apparatus according to an embodiment of the present invention;

FIG. 2 is a block diagram of a control configuration of an ultrasonic imaging apparatus according to an embodiment of the present invention;

FIG. 3 is a block diagram of a control configuration of an image processor according to an embodiment of the present invention;

FIG. 4 illustrates light paths when a light source is located to face a viewpoint with an object in between;

FIG. 5 illustrates an example of a texture image including information about a translucency property and multi-layer tissue of an object;

FIG. 6 is a view for describing a process of rearranging the position of an object with respect to a viewpoint upon sampling, according to an embodiment of the present invention;

FIG. 7 is a view for describing a method of calculating the location of a pixel of a texture image, corresponding to each sample, according to an embodiment of the present invention;

FIGS. 8A, 8B, and 8C are views for describing a method of calculating a depth from a surface to each sample with respect to a viewpoint, according to an embodiment of the present invention;

FIG. 9 is a flowchart of a method of calculating a depth from an object's surface to each sample with respect to a viewpoint, according to an embodiment of the present invention;

FIGS. 10A and 10B are views for describing a method of calculating a depth from a surface to each sample with respect to a light source, according to an embodiment of the present invention;

FIG. 11 is a flowchart of a method of calculating a depth from an object's surface to each sample with respect to a light source, according to an embodiment of the present invention; and FIG. 12 is a flowchart of a rendering algorithm for a volume rendering method, according to an embodiment of the present invention.

BEST MODE FOR CARRYING OUT THE INVENTION

Reference will now be made in detail to the embodiments of the present invention, examples of which are illustrated in the accompanying drawings, wherein like reference numerals refer to like elements throughout.

FIG. 1 is a perspective view of an ultrasonic imaging apparatus according to an embodiment of the present invention. Referring to FIG. 1, the ultrasonic imaging apparatus may include a main body 100, an ultrasonic collector 110, an input unit 150, a main display unit 160, and a sub display unit 170.

In one side of the main body 100, one or more female connectors 145 may be provided. A male connector connected to a cable 130 may be physically coupled with one of the female connectors 144.

In the bottom of the main body 100, a plurality of castors (not shown) for moving the ultrasonic imaging apparatus may be provided. The plurality of castors may be used to fix the ultrasonic imaging apparatus at a specific location and to move it in a specific direction.

The ultrasonic collector 110 contacts the skin surface of an object, and may transmit or receive ultrasonic waves. More specifically, the ultrasonic collector 110 functions to irradiate transmission signals (that is, ultrasonic signals) received from the main body 100 to the inside of the object, receive ultrasonic echo signals reflected from a specific part of the object, and transfer the ultrasonic echo signals to the main body 100. The ultrasonic collector 110 may be connected to one end of the cable 130, and the other end of the cable 130 may be connected to the male connector 140. The male connector 140 connected to the other end of the cable 130 may be physically coupled with one of the female connectors 145 of the main body 145.

The input unit 150 is used to receive commands for instructing operations of the ultrasonic imaging apparatus. For example, a mode selection command, such as an Amplitude mode (A-mode), a Brightness mode (B-mode), or a Motion mode (M-mode), or an ultrasonography start command may be input through the input unit 150. A command input through the input unit may be transferred to the main body 100 through wired/wireless communication.

The input unit 150 may include at least one of a keyboard, a foot switch, and a foot pedal. The keyboard may be implemented with hardware, and disposed on the upper part of the main body 100. The keyboard may include at least one(s) of a switch, keys, a joystick, and a trackball. As another example, the keyboard may be implemented with software as a graphic user interface (GUI). In this case, the keyboard may be displayed through the sub display unit 170 or the main display unit 160. The foot switch or the foot pedal may be provided in the lower part of the main body 100, and an operator may control operations of the ultrasonic imaging apparatus using the foot pedal.

An ultrasonic collector holder 120 for accommodating the ultrasonic collector 110 may be provided to be adjacent to the input unit 150. There may be provided one or more ultrasonic collector holders. The operator may put the ultrasonic collector 110 into the ultrasonic collector holder 120 to safely keep the ultrasonic collector 110 when he/she does not use the ultrasonic imaging apparatus.

The sub display unit 170 may be installed in the main body 100. FIG. 1 shows a case in which the sub display unit 170 is provided on the upper part of the input unit 150. The sub display unit 170 may display applications related to operations of the ultrasonic imaging apparatus. For example, the sub display unit 170 may display menus or guidance for ultrasonography. The sub display unit 170 may be implemented as a Cathode Ray Tube (CRT) or a Liquid Crystal Display (LCD).

The main display unit 160 may be also installed in the main body 100). FIG. 1 shows a case in which the main display unit 160 is positioned above the sub display unit 170. The main display unit 160 may display ultrasonic images acquired by ultrasonography. The main display 160 may be, like the sub display 170, implemented as a CRT or a LCD.

In FIG. 1, the main display unit 160 is integrated with the main body 100, however, the main display unit 160 may be separated from the main body 100.

In the embodiment of FIG. 1, the ultrasonic imaging apparatus includes both the main display unit 160 and the sub display unit 170, however, the sub display unit 170 may be omitted. In this case, applications, menus, etc., which are displayed through the sub display unit 170, may be display through the main display unit 160.

FIG. 2 is a block diagram of a control configuration of an ultrasonic imaging apparatus according to an embodiment of the present invention. Referring to FIGS. 1 and 2, the ultrasonic collector 110 includes a plurality of ultrasonic transducers 114 to generate ultrasonic waves according to alternating current applied from a power source 112, to irradiate the ultrasonic waves to an object, to receive echo ultrasonic waves reflected from a target part of the object, and to convert the received echo ultrasonic waves into electrical signals. The power source 112 may be an external power supply, or a power storage unit included in the ultrasonic imaging apparatus.

Each ultrasonic transducer 114 may be a magnetostrictive ultrasonic transducer using the magnetostrictive effect of a magnetic material, a piezoelectric ultrasonic transducer using the piezoelectric effect of a piezoelectric material, or a capacitive micromachined ultrasonic transducer (CMUT) that transmits and receives ultrasonic waves using vibration of several hundreds or thousands of micromachined thin films.

When alternating current from the power source 112 is applied to each ultrasonic transducer 114, the piezoelectric vibrator or thin film of the ultrasonic transducer 114 vibrates, thus generating ultrasonic waves. The generated ultrasonic waves are irradiated to an object, for example, to the inside of a human body. The irradiated ultrasonic waves are reflected by one or more target areas that may be located at different depths from the surface of the object. The ultrasonic transducers 114 receive ultrasonic echo signals reflected from the target areas, and convert the received ultrasonic echo signals into electrical signals to obtain a plurality of received signals.

The received signals are transferred to the main body 100 through a wired/wireless communication network. Since the ultrasonic collector 110 receives the ultrasonic echo signals through a plurality of channels, the plurality of received signals are also transferred to the main body 100 through a plurality of channels.

The main body 100 may include a beamformer 210, a volume data generator 220, and an image processor 230. In another embodiment, one or more components of the above-mentioned components may be omitted.

The beamformer 210 may perform beamforming based on the plurality of received signals. Beamforming is operation of focusing a plurality of received signals received through a plurality of channels to acquire a proper ultrasonic image about the inside of an object.

The beamformer 210 corrects time differences of a plurality of received signals, caused by distance differences between the respective transducers 114 and a target area of the object. Then, the beamformer 210 enhances a plurality of received signals corresponding to specific channels, or relatively attenuates a plurality of received signals corresponding to other channels, thereby focusing the plurality of received signals. At this time, the beamformer 210 may enhance or attenuate a specific received signal by selectively allocating predetermined weights to a plurality of received signals received through individual channels.

The beamformer 210 may focus a plurality of received signals collected by the ultrasonic collector 110, for each frame, in consideration of the locations and focusing points of the transducers 114 of the ultrasonic collector 110.

The beamforming that is performed by the beamformer 210 may be one of data-independent beamforming and adaptive beamforming.

The volume data generator 220 generates ultrasonic image data based on the signals focused by the beamformer 210. If the beamformer 210 focuses a plurality of received signals for each of a plurality of frames, the volume data generator 220 generates a plurality of pieces of ultrasonic image data respectively corresponding to the respective frames based on a plurality of focused signals. The ultrasonic image data may be 3D ultrasonic image data for the object, that is, volume data for the object.

The image processor 230 may receive the volume data for the object from the volume data generator 230. Then, the image processor 230 performs volume rendering on the volume data, and transfers the results of the volume rendering to the main display unit 160 so that the main display unit 160 can output the results of the volume rendering as images.

The image processor 230 may volume-render the 3D volume data using one of volume rendering methods well-known in the art. In detail, volume rendering may be classified into surface rendering and direct volume rendering.

The surface rendering is to extract surface information from volume data based on predetermined scalar values and amounts of spatial changes, to convert the surface information into a geometric factor, such as a polygon or a surface patch, and then to apply a conventional rendering technique to the geometric factor. Examples of the surface rendering are a marching cubes algorithm and a dividing cubes algorithm.

The direct volume rendering is to directly render volume data without converting volume data into a geometric factor. The direct volume rendering is useful to represent a translucent structure since it can visualize the inside of an object as it is. The direct volume rendering may be classified into an object-order method and an image-order method according to a way of approaching volume data.

The image-order method is to sequentially decide pixel values of an image. An example of the image-order method is volume ray casting. According to the volume ray casting, as illustrated in FIG. 6, a virtual ray is irradiated from a specific viewpoint toward a predetermined pixel of a display screen, and then voxels through which the virtual ray has been transmitted from among voxels of volume data are detected. Then, brightness values of the detected voxels are accumulated to decide a brightness value of the corresponding pixel of the display screen. Alternatively, an average value of the detected voxels may be decided as a brightness value of the corresponding pixel of the display screen. Also, a weighted average value of the detected voxels may be decided as a brightness value of the corresponding pixel of the display screen.

The object-order method is to directly project volume data on an image. An example of the object-order method is splatting. According to splatting, by aligning the center of a reconfigured kernel with a point at which a voxel is projected on a plane to be observed, and then causing peripheral pixels to distribute values to the voxel, a brightness value of the corresponding pixel is decided.

If the volume rendering is completed, a 3D ultrasonic image may be produced. Each pixel of the 3D ultrasonic image may have a brightness value and a color value. The following description is given under an assumption that the volume ray casting of the above-mentioned volume rendering methods is used.

Referring again to FIG. 2, the storage unit 240 may store data or algorithms required for operations of the ultrasonic imaging apparatus 200. For example, the storage unit 240 may store an algorithm for rendering volume data, an algorithm for calculating the location of a sample with respect to a viewpoint, and an algorithm for calculating a depth from a surface to each sample.

The storage unit 240 may be Read Only Memory (ROM), Random Access Memory (RAM), Programmable Read Only Memory (PROM), Erasable Programmable Read Only Memory (EPROM), a non-volatile memory device such as flash memory, a volatile memory device such as Random Access Memory (RAM), or an optical disk. However, the storage unit 280 is not limited to these, and may be any other storage device well-known in the art.

An embodiment in which the main body 100 of the ultrasonic imaging apparatus includes the beamformer 210, the volume data generator 220, the image processor 230, and the storage unit 240 has been described above with reference to FIGS. 1 and 2. However, the main body 100 does not need to include all the above-mentioned components. In other words, some of the components may be included in another component, for example, in the ultrasonic collector 110.

For example, the ultrasonic collector 110 may include the beamformer 210 to produce an ultrasonic image based on electrical signals, and to correct the produced ultrasonic image.

The above description relates to the appearance and control configuration of an ultrasonic imaging apparatus according to an embodiment of the present invention. Hereinafter, a control configuration of the image processor 230 of the ultrasonic imaging apparatus, and the functions of the individual components of the ultrasonic imaging apparatus will be described in more detail with reference to FIGS. 3 to 12.

FIG. 3 is a block diagram of a control configuration of the image processor 230 according to an embodiment of the present invention. Referring to FIG. 3, the image processor 230 may include a texture image storage unit 232, a sampling unit 234, a calculator 236, and a data accumulating unit 238.

The texture image storage unit 232 may store texture images that are referred to upon volume rendering. The texture image storage unit 232 may be implemented as the same type of device as the storage unit 240 since the texture image storage unit 232 also functions to store data.

The texture image storage unit 232 may store one or more texture images. A texture image that is to be stored in the texture image storage unit 232 may reflect a translucency property or multi-layer tissue of an object. Hereinafter, a translucency property or multi-layer tissue of an object will be described.

A phenomenon in which light is transmitted through a certain object without being absorbed in or reflected from the object is called transmission. A degree of light transmission greatly depends on the properties of an object through which the light is transmitted. For example, a transparent material such as glass transmits a major part of incident light although it reflects a small amount of the incident light and absorbs a small amount of the incident light. A degree at which light is transmitted through a material is determined as transparency of the material, and a material through which light is 100% transmitted can be considered to have transparency. Meanwhile, a material through which no light is transmitted is considered as an opaque material. If a certain material transmits a small amount of light, and scatters light according to its surface structure and properties to lower transparency, the material is considered to have a translucency property.

An object such as the fetus having soft tissue can be considered to have a translucency property since a constant amount of light can be transmitted through the object. Accordingly, such an object is strongly dependent on an effect due to a translucency property since a part of light irradiated from a light source is transmitted deeply to tissue. In the case of an object having a translucency property, an effect due to light transmission through the object must be considered even when a light source is positioned behind the object, as well as when a light source is positioned in front of the object. A translucency property can be represented through calculations under an assumption that a part of incident light is transmitted through the inside of an object while the remaining part of the incident light is reflected from the surface of the object.

FIG. 4 illustrates light paths when a light source is located to face a viewpoint with an object in between. In FIG. 4, no path of light reflected from the object is shown since the reflected light has no influence in observing the object at the viewpoint. First, a path of light passing a point df1 at which light from a light source enters the inside of the object, and a point do1 at which the light transmitted through the inside of the object is escaped from the object is described below. The light is transmitted through the inside of the object by a distance of S1. Meanwhile, when light generated from a light source is transmitted through an object having a non-uniform thickness, a distance by which the light is transmitted through the inside of the object depends on a path of the light.

Referring to FIG. 4, a distance S1 by which light is transmitted through the lower part of the object is longer than a distance S2 by which light is transmitted through the upper part of the object (S1>S2). A part of light incident to an object is absorbed in the object when the light is transmitted through the inside of the object, so long as the object is not a completely transparent material. Accordingly, as a distance by which light is transmitted through the inside of an object is longer, the more amount of light is absorbed in the object. Therefore, in the case of FIG. 4, when the object is seen from the viewpoint, the point do1 is observed darker than the point do2. That is, an area having the deeper depth from the surface of an object which a light source faces must be represented darker than an area having the shallower depth from the surface of the object which the light source faces in order to improve the reality of the object. In consideration of this, one axis of a texture image that is to be stored in the texture image storage unit 232 may be configured to represent a depth from a surface of an object which a light source faces.

With the translucency property of an object, multi-layer tissue of the object must be considered. Light transmitted through a medium is influenced by the kind of the medium. Specifically, since different kinds of mediums absorb different wavelengths of light, the color of an object shown from a viewpoint depends on a depth to which light has been transmitted through the object. Accordingly, when an object is shown from a viewpoint, the effect of light transmitted through different material layers of the object, that is, the colors of light transmitted through the different material layers of the object are mixed and visually shown.

For example, if an object is a human body, multi-layer tissue of the human body can be considered. The reason is because the skin of a human body is not a single material and consists of several different kinds of layers. If the skin of the human body is divided into a horny layer, an epidermis layer, a dermis layer, and a panniculus layer, the object may be represented in a different way from an object having a single layer since the respective layers have different properties. Accordingly, when an object has multi-layer tissue like the skin of a human body, the multi-layer tissue of the object is considered upon rendering in order to improve reality. Particularly, in the case of volume rendering, since the inside of an object as well as the surface of the object must be rendered, a method of deciding color values in consideration of multi-layer tissue of an object can improve the reality of rendering.

In order to consider multi-layer tissue of an object, what layer of the object a sample is located in needs to be determined. In order to determine a layer to which a sample belongs, a depth at which a sample is located from a surface with respect to a viewpoint may be calculated. By deciding a color value in consideration of the depth of a sample upon rendering, reality can be improved. In order to reflect the depths of samples to a texture image, one axis of the texture image may be configured to represent a depth from a surface with respect to a viewpoint.

FIG. 5 illustrates an example of a texture image including information about a translucency property and multi-layer tissue of an object (e.g., the fetus). In the following description, a texture image, which is shown as black and white in FIG. 5, is assumed to be in color since the present disclosure is implemented using a color texture image.

The texture image storage unit 232 (see FIG. 3) may store 2-dimensional (2D) texture images. Each of the 2D texture images may be configured with a group of texels each having a brightness value or a color value. When rendering is performed, the brightness or color values of the texels may be referred to in order to improve reality. The texel is a minimum unit constructing text image data.

Referring to FIG. 5, a texture image may be configured such that the horizontal axis represents the depths of samples from a surface with respect to a viewpoint, and the vertical axis represents the depths of the samples from a surface with respect to a light source. As described above, the depth (the horizontal axis of a texture image) of a sample from a surface with respect to a viewpoint is used to determine what layer of the corresponding object the sample is located in, and accordingly, the horizontal axis of the texture image may become criteria to decide a color value of a texel. Also, the depth (the vertical axis of a texture image) of a sample from a surface with respect to a light source is used to determine a depth to which light has been transmitted through the corresponding object, and accordingly, the vertical axis of the texture image may become criteria to decide a brightness value of a texel.

Referring again to FIG. 3, the sampling unit 234 receives volume data of an object from the volume data generator 220 (see FIG. 2). The sampling unit 234 performs sampling for volume rendering on the received volume data.

Upon sampling, the position of the object may be rearranged with respect to a viewpoint in order to facilitate calculations for volume rendering. Specifically, axes of a display screen may be set to axes of an orthogonal coordinates system, and the locations of samples may be represented as vectors. Thereby, distances between samples and a surface may be obtained through a simple mathematical calculation.

FIG. 6 is a view for describing a process of rearranging the position of an object with respect to a viewpoint upon sampling, according to an embodiment of the present invention. FIG. 6 shows an example of an arrangement of volume data samples, having a cube shape in which each side has scalar values of N voxels. Each voxel is represented in the form of $\vec{i}=(i,j,k)$, and a voxel value of the vector $\vec{i}$ is $F(\vec{i})$, wherein f is a function representing a voxel value corresponding to a voxel. First, it is assumed that light beams are projected from an observer toward volume data. In this case, a display screen is configured with M×N pixels, wherein M is the number of pixels arranged on the horizontal axis of the display screen, and N is the number of pixels arranged on the vertical axis of the display screen. Each light beam is projected to a pixel. Each pixel or a light beam projected through each pixel is represented as a vector $\vec{u}=(u,v)$, wherein u and v are coordinates on x- and y-axis, and points that are sampled on the light beams are represented as $\vec{U}=(u,v,w)$, wherein w is a coordinate on the z-axe. The z-axis coordinate w of the vector $\vec{U}$ increases in proportion to a sampling distance and the number of times of sampling.

By obtaining the vector $\vec{U}$, the locations of samples can be acquired. By representing the locations of samples as vectors, distances of the samples to a surface can be easily acquired by a mathematical calculation.

Setting values for sampling that is performed by the sampling unit 234 may be input by a user through the input unit 150. For example, a sampling distance, the number of times of sampling, and a point at which sampling terminates may be set to desired values by a user.

Referring again to FIG. 3, the calculator 236 receives the location of each sample, acquired by sampling, from the sampling unit 234. The calculator 236 functions to calculate a distance of the sample to the surface, using the received location of the sample. In order to increase the speed and accuracy of calculation, the calculator 236 may be implemented with hardware to enable parallel processing using a plurality of pipelines.

The calculator 236 may perform a calculation for detecting a texel corresponding to each sample in the direction of the light beam passing through the display screen. Referring to FIG. 6, the horizontal axis of the texture image may be set to a depth from a surface with respect to a viewpoint, and the vertical axis of the texture image may be set to a depth from a surface with respect to a light source. By calculating a value of the sample on the horizontal or vertical axis of the texture image using the sample location received from the sampling unit 234, the corresponding texel can be detected. The calculator 236 may transfer a brightness value or a color value of the detected texel to the data accumulating unit 238.

FIG. 7 is a view for describing a method of calculating the location of a texel corresponding to each sample, according to an embodiment of the present invention. In order to obtain a color value of each sample of an object, to which multi-layer tissue of the object has been reflected, a depth X of the corresponding sample from a surface with respect to a viewpoint is calculated. Also, in order to obtain a brightness value of each sample of an object, to which the translucency property of the object has been reflected, a depth Y of the corresponding sample from a surface with respect to a light source is calculated. Based on the resultant coordinate value (x, y), a texel corresponding to the sample may be detected from the texture image of FIG. 6. The calculator 236 may transfer the color value and brightness value of the detected texel to the data accumulating unit 238. Hereinafter, a method of calculating the depths X and Y will be described in detail with reference to FIGS. 8 to 11.

FIGS. 8A, 8B, and 8C are views for describing a method of calculating a depth X from a surface to each sample with respect to a viewpoint, according to an embodiment of the present invention. Referring to FIG. 8A, when a virtual light beam is projected to an object from a viewpoint, volume data is sampled in the direction of the light beam. In order to find a surface on the path of the light beam, sampling from the viewpoint continues to be performed, and if it is found a first sample which is not an empty space, the location of the found sample is estimated as the location of a surface. If an empty space is found during continuous sampling, the location of a sample which is not an empty space and is first found is again estimated as the location of a surface.

Referring to FIG. 8B, a gradient vector of the estimated surface is calculated. The gradient vector of the surface is calculated using texel values of peripheral samples on x-, y-, and z-axis. The following Equation (1) is used to calculate an x component of a gradient vector of a surface. In Equation (1), a vector represents the location of a sample, f represents a voxel value of the sample, and h represents a unit distance between samples, wherein u, v, and w are x-, y-, and z-axis coordinates.

$$g_x(\vec{U}_{(u,v,w)}) = \frac{f(\vec{U}_{(u+1,v,w)}) - f(\vec{U}_{(u-1,v,w)})}{2h} \quad \text{Equation (1)}$$

Referring to FIG. 8C, a plane in which the normal vector is the gradient vector of the surface is obtained. The plane is a tangential plane of the object at a point corresponding to the surface. A distance from the plane to the sample of which a depth has to be calculated is calculated, and the distance becomes a depth X from the surface to the sample with respect to the viewpoint.

FIG. 9 is a flowchart of a method of calculating a depth X from an object's surface to each sample with respect to a viewpoint, according to an embodiment of the present invention. The depth X can be calculated by obtaining a tangential plane at a point corresponding to the surface, and calculating a distance from the tangential plane to the sample.

First, sampling is performed along a light beam from a viewpoint (300). At this time, the number of times of sampling increases in proportion to a degree of reality of volume rendering. The reason is because as the number of times of sampling is more, the more accurate location of a surface can be found. The number of times of sampling may be set to a value input by a user through the input unit 150 (see FIG. 2). Sampling may be performed simultaneously with or separately from the following process, and in the following description, it is assumed that sampling is performed simultaneously with the following process.

Successively, voxel values of samples are checked in order from the viewpoint (310). Then, it is determined whether each sample is an empty space based on the voxel values (320). Whether each sample is an empty space may be determined using an Opacity Transfer Function (OTF) that defines the relationship between density values and transparency among the voxel values. Since a method of determining an empty space using an OTF is well-known in the art, further descriptions will be omitted.

If a sample is an empty space, the next sample is checked (325). If a sample which is not an empty space is found, the location values of the sample are acquired (330). The sample whose location values have been acquired is estimated as a surface. The reason is because a sample which is not an empty space and is first found is a first sample that exists in the inside of the object in the direction of the light beam.

Then, operation for calculating a depth X of the sample is performed. The depth X of the sample is calculated using the location values of the sample. To do this, operation of calculating a gradient vector at the location of the sample is performed (340). The gradient vector is calculated using peripheral values on the x-, y-, and z-axis of the sample. Since a method of calculating the gradient vector has been described above with reference to FIG. 8B, further descriptions will be omitted.

After the gradient value is calculated, a plane on which the location of the sample estimated as the surface exists and in which the normal vector is the gradient vector of the surface is obtained (350). The plane is a tangential plane of the object at a point corresponding to the surface since the plane meets the object only at the point of the surface and is perpendicular to the object. By using the tangential plane which is perpendicular to the object, the depths of samples can be easily calculated in the direction of the light beam.

Finally, by calculating a distance between the tangential plane and the sample of which the depth X has to be calculated, the depth X of the sample from the surface with respect to the viewpoint may be acquired (360). The depth X may be used to detect a texel on the horizontal axis of the texture image of FIG. 6.

FIGS. 10A, 10B, and 10C are views for describing a method of calculating a depth Y from a surface to each sample with respect to a light source, according to an embodiment of the present invention. Referring to FIG. 10A, a light beam advancing from a sample of which a depth has to be calculated toward a light source is generated. This is aimed at calculating a distance by which light irradiated from a light source is transmitted through a medium until the light arrives at the corresponding sample to reflect the translucency property of the corresponding object. Since light reflected from the surface of the object has no influence in deciding a brightness value of the sample, only light advancing straightly is considered.

Referring to FIG. 10B, volume data is sampled at regular time intervals along the generated light beam. At this time, sampling is performed along the traveling direction of the light beam, starting from the sample of which the depth has to be calculated, so that brightness values among voxel values of samples are checked. Since a brightness value becomes greater as light irradiated from a light source is transmitted through a medium to the deeper depth, the brightness values are checked to detect a sample on the surface of a medium. The brightness values acquired in order of sampling are compared to a predetermined threshold value. Since a point having a great change in brightness values can be considered as a point at which light starts to be transmitted through a medium, if the brightness value of a certain sample falls below the predetermined threshold value, the previous sample may be estimated as a surface. Then, a distance between the surface and the sample of which the depth has to be calculated is calculated, so that a depth Y from the surface to the sample can be calculated.

FIG. 11 is a flowchart of a method of calculating a depth Y from an object's surface to each sample with respect to a light source, according to an embodiment of the present invention. The depth Y can be calculated based on a fact that the strength of light varies depending on a distance by which the light is transmitted through a medium until the light arrives at a sample.

In order to calculate the depth Y, first, a light beam advancing from a sample of which a depth has to be calculated toward a light source is generated (400). This is aimed at setting a path of light arriving at the corresponding sample from an actual light source, and easily calculating a distance by which the light advancing along the path is transmitted through a medium.

After the light beam is generated, sampling is performed at regular time intervals along the traveling direction of the generated light beam (410). At this time, the number of times of sampling increases in proportion to a degree of reality of volume rendering. The reason is because as the number of times of sampling is more, the more accurate location of a surface can be found. The number of times of sampling may be set to a value input by a user through the input unit 150 (see FIG. 2). Sampling may be performed simultaneously with or separately from the following process, and in the following description, it is assumed that sampling is performed simultaneously with the following process.

If sampling is performed, brightness values among voxel values of samples are acquired in order, starting from a sample located most distant from the light source (420), and the brightness values are compared to a predetermined threshold value (430). By comparing the brightness values to the predetermined threshold value, it can be determined whether a sample is included in the inside of the object. The predetermined threshold value may be set to an appropriate value within an error range of a brightness value when light is not transmitted through any medium.

When the brightness value of a sample is compared to the predetermined threshold value, if the brightness value of the sample is greater than the predetermined threshold value, the corresponding sample is determined as a sample located in the inside of the object, and then, the next sample is compared to the predetermined threshold value (435). Meanwhile, if the brightness value of the sample is smaller than the predetermined threshold value, the sample is determined as a sample located outside the object.

If a sample is determined as a sample located outside the object, the previous sample is estimated as a surface of the object. Then, the location values of the sample are acquired (440). The reason is because if a sample located outside the object is found after successive samples located in the inside of the object are found, the previous sample of the sample located outside the object is a final sample located in the inside of the object in the traveling direction of the light beam.

Then, a distance from the surface to the sample of which the depth has to be calculated is calculated, so that a depth Y from the surface to the sample can be calculated (450). The depth Y may be used to detect a texel on the vertical axis of the texture image of FIG. 6.

Referring to FIGS. 3 and 11, the calculator 236 may detect a texel corresponding to the sample from a texture image stored in the texture image storage unit 232 based on the resultant depth value (x, y). Then, a brightness value or a color value is detected from the corresponding texel.

The data accumulating unit 238 receives the brightness value or the color value of the texel detected by the calculator 236. The brightness values or color values of texels corresponding to samples acquired along the path of a light beam passing through a display pixel with respect to a viewpoint are all accumulated in the data accumulating unit 238. Based on the values accumulated in the accumulating unit 238, the brightness or color of the display pixel through which the light beam passes is decided.

FIG. 12 is a flowchart of a rendering algorithm for a volume rendering method, according to an embodiment of the present invention.

First, sampling is performed at regular time intervals in the direction of a light beam from a viewpoint (500). At this time, as sampling is performed at shorter time intervals, more samples are subject to a calculation to decide a brightness value and a color value of each display pixel. Accordingly, since more brightness values and color values of texels are acquired, a more amount of data is accumulated to obtain the results of rendering having high reality. A sampling interval may be set to a value input by a user through the input unit 150.

Then, voxel values of samples are checked in order, starting from a sample located closest to a viewpoint (510). Then, it is determined whether each sample is an empty space (520). Whether the sample is an empty space may be determined using the OTF which is well-known in the art. If it is determined that a sample is an empty space based on the voxel value of the sample, it is determined whether the next sample is an empty space (525). The reason is because a sample corresponding to an empty space has no information about an object.

If a sample which is not an empty space is found, the location values of the sample are acquired (530), and a calculation for detecting a texel corresponding to the sample from a texture image is performed. To do the calculation, a depth of the sample from a surface of the object with respect to a light source is calculated (540), and a depth of the sample from a surface of the object with respect to the viewpoint is calculated (550).

The depth of the sample from the surface of the object with respect to the light source is calculated by calculating a distance by which a light beam generated from the sample passes through a medium until the light beam arrives at the light source. The depth of the sample from the surface of the object with respect to the viewpoint is calculated by estimating a sample which is not an empty space and is first found as a surface, and calculating a distance between a tangential plane of the object at a point corresponding to the surface and the sample of which the depth has to be obtained. Operation of calculating the depth of the sample from the surface of the object with respect to the light source may be performed simultaneously with or separately from operation of calculating the depth of the sample from the surface of the object with respect to the viewpoint.

Based on the results of the calculations, the corresponding texel is detected from a texture image stored in the texture image storage unit 232. The texture image can have brightness values and color values to which a translucency property and multi-layer tissue of the object have been reflected. A brightness value to which a translucency property has been reflected can be obtained by calculating a depth from a surface of an object to a sample of which a depth has to be obtained with respect to a light source, and detecting the corresponding texel. A color value to which multi-layer tissue has been reflected can be obtained by calculating a depth from a surface of an object to a sample of which a depth has to be obtained with respect to a viewpoint, and detecting the corresponding texel. In this way, the brightness and color values of the texel are obtained (560).

The obtained brightness and color values are accumulated in existing values, thereby performing rendering (570). Accordingly, the brightness and color values of a display pixel are decided by accumulating the brightness and color values of texels corresponding to samples sampled along a light beam passing through the corresponding display pixel.

After the brightness and color values are accumulated, it is determined whether sampling needs to continue to be performed (580). If sampling needs to continue to be performed, the location of the next sample is acquired, and the above-described operation is performed on the next sample. If sampling does no longer need to continue to be performed, the process terminates.

The invention claimed is:

1. An ultrasonic imaging apparatus comprising:
    an ultrasonic collector configured to collect ultrasonic waves from an object;
    a volume data generator configured to generate volume data based on the ultrasonic waves;
    a storage that stores a texture image; and
    an image processor configured to perform volume rendering on the volume data with reference to the texture image,
    wherein the texture image is a two-dimensional image, and a translucency property and a multi-layer tissue property of the object are reflected to each texel of the texture image, and
    wherein one axis of the texture image represents a depth from a surface of the object which a light source faces, and another axis of the texture image represents a depth from a surface of the object with respect to a viewpoint,
    wherein the image processor is further configured to:
        acquire a sample by sampling the volume data,
        acquire a depth X of the sample from the surface of the object with respect to the viewpoint and a depth Y of the sample from the surface of the object with respect to the light source, and
        detect a texel corresponding to the sample from the texture image based on the depth X and the depth Y.

2. The ultrasonic imaging apparatus according to claim 1, wherein each texel to which the translucency property of the object has been reflected has a brightness value varying depending on the depth Y from the surface of the object with respect to the light source.

3. The ultrasonic imaging apparatus according to claim 1, wherein each texel to which the multi-layer tissue of the object has been reflected has a color value varying depending on the depth X from the surface of the object with respect to the viewpoint.

4. The ultrasonic imaging apparatus according to claim 1, further comprising a display configured to display a volume-rendered ultrasonic image produced by the image processor.

5. A control method of an ultrasonic imaging apparatus, comprising:
    collecting ultrasonic waves from an object;
    generating volume data based on the ultrasonic waves;
    storing a texture image; and
    performing volume rendering on the volume data with reference to the texture image,
    wherein the texture image is a two-dimensional image, and a translucency property and a multi-layer tissue property of the object are reflected to each texel of the texture image, and
    wherein one axis of the texture image represents a depth from a surface of the object which a light source faces, and another axis of the texture image represents a depth from a surface of the object with respect to a viewpoint,
    wherein the performing volume rendering comprises:
        acquiring a sample by sampling the volume data,
        acquire a depth X of the sample from the surface of the object with respect to the viewpoint and a depth Y of the sample from the surface of the object with respect to the light source, and
        detecting a texel corresponding to the sample from the texture image based on the depth X and the depth Y.

6. The control method according to claim 5, wherein each texel to which the translucency property of the object has been reflected has a brightness value varying depending on the depth Y from the surface of the object with respect to the light source.

7. The control method according to claim 5, wherein each texel to which the multi-layer tissue of the object has been reflected has a color value varying depending on the depth X from the surface of the object with respect to the viewpoint.

8. The control method according to claim 5, further comprising displaying an ultrasonic image produced by the volume rendering.

* * * * *